United States Patent [19]

Freitag

[11] 4,008,802
[45] Feb. 22, 1977

[54] SURGICAL NEEDLE RETAINING AND INVENTORY PAD, AND ACCOUNTING METHOD

[75] Inventor: Samuel L. Freitag, Oakland, Calif.

[73] Assignee: Acura-Med, San Leandro, Calif.

[22] Filed: May 19, 1975

[21] Appl. No.: 578,714

[52] U.S. Cl. .......................... 206/63.3; 150/52 R; 206/382; 206/459; 206/460
[51] Int. Cl.² ...................................... A61L 17/02
[58] Field of Search ......... 150/52 R; 206/380, 382, 206/365, 366, 406, 435, 460, 438, 459, 63.3

[56] References Cited

UNITED STATES PATENTS

| 670,096 | 3/1901 | Brabant | 206/382 |
|---|---|---|---|
| 1,106,773 | 8/1914 | Brabant | 206/380 |
| 1,581,422 | 4/1926 | Bergen | 206/380 |
| 3,727,658 | 4/1973 | Eldridge | 150/52 R |

FOREIGN PATENTS OR APPLICATIONS 1,375,109  9/1964  France ................. 206/380

*Primary Examiner*—Ro E. Hart
*Attorney, Agent, or Firm*—Julian Caplan

[57] ABSTRACT

A pad of resilient material through which needles can be inserted is provided with consecutively numbered needle receiving zones formed by ridges upstanding from an upper face of the pad, and by transversely extending lines across the ridges. This enables an accurate method of counting the needles used in the surgery because a needle used by the surgeon can be positioned in a zone by insertion through the adjacent ridge enabling an accurate count of the needles by merely glancing at the pad.

5 Claims, 8 Drawing Figures

SURGICAL NEEDLE RETAINING AND INVENTORY PAD, AND ACCOUNTING METHOD

BACKGROUND OF THE INVENTION

In surgery, surgical needles are dispensed to the surgeon and an accurate count is maintained to insure that after the patient is ready for closing the number of needles used in the surgery is the same as those that have been dispensed to the surgeon. Pads for holding the needles as well as other instruments after they have been used are known in the art as is typified by the patent to Eldridge, Jr. U.S. Pat. No. 3,727,658, dated Apr. 17, 1973, wherein the pad is provided with magnetic strips on its upper face to retain metallic instruments used in surgery, such as surgical needles.

However, such type of magnetic retaining means is not all to be desired because instruments used in the surgery which are not intended to be retained by the pad, such as needle holders may become attracted to the pad by the magnetic strips, and when pulled away may knock off implements adhered to the pad by such magnets. Moreover, there is no systematic arrangement of the used surgical needles so that an accurate count may be obtained at a glance of the number of needles that have been used in the surgery to insure that the correct number has been accounted for before the patient is closed.

SUMMARY AND OBJECTS OF THE INVENTION

Summarizing the invention hereof, it comprises a pad which has projecting from its upper face, ridges of resilient flexible material which are adapted to have inserted therein surgical needles so as to fixedly retain them. The face is also provided with a plurality of needle receiving zones adjacent the respective ridges; and these zones are marked with numbers which run consecutively from number 1 through the number designating the total number of zones.

As the needles are used they are positioned consecutively in the needle retaining zones; and when the surgery is over and the patient is about to be closed, the scrub nurse or whoever else keeps track of the number of needles that have been dispensed to the surgeon, can thus tell at a glance whether the correct number of used needles has been accounted for. Desirably the zones are formed by side by side, desirably parallel, ridges projecting upwardly from the upper face of the pad and by lines, desirably parallel, marked on such surfaces, and which extend transversely across the ridges. This, thus provides continuous ridges with a ridge portion adjacent each zone into which the needle can be inserted and fixedly held.

Advantageously, the pad and the ridges thereon are integrally formed either by molding or by cutting, and are desirably of soft elastomeric material, such as foam polyurethane. As a reinforcement, the back surface of the pad is attached by an adhesive bond to a relatively stiff but still flexible backing sheet, preferably of paperboard. This gives body to the pad. The exposed back surface of the backing sheet has strips of pressure sensitive tape secured thereto which are covered by masking strips so that when the masking strips are removed the pad may be fixedly adhered to the so-called "field" (support table) in the surgery room.

Also, a line of weakness, desirably a perforated line is formed in the backing sheet to enable the pad to be readily folded on itself with the needle supporting faces facing each other. A similar strip of pressure sensitive tape is attached to the front face of the pad adjacent one edge thereof, and is covered with a masking strip. When the masking strip is removed, the edges of the pad adjacent the pressure sensitive strip can be adhered together when the pad is folded so that the pad may be disposed of in folded condition with the used needles covered.

From the preceding it is seen that the invention has as its objects, among others, the provision of an improved surgical needle retaining and inventory pad from which an accurate count of the needles used in surgery can be obtained before the patient is closed, which is of simple and economical construction, and which enables an improved method of maintaining an inventory of surgical needles used during the surgery to insure that the patient is not closed until all the needles are accounted for. Other objects of the invention will become apparent from the following more detailed description and accompanying drawings, in which:

DETAILED DESCRIPTION

Pad 2 is desirably of rectangular shape; and comprises a base sheet 3 having spaced apart, desirably parallel, ridges 4 projecting upwardly from the upper face of the sheet. Extending transversely at right angles across the upper face of the sheet and the ridges, are spaced apart parallel lines 6 which together with the ridges divide the pad into a plurality of side by side rows R of needle receiving zones indicated by reference letter Z. These zones are marked consecutively with numbers from number 1 through the number designating the total number of zones, namely 40, on the pad.

Figure 1:
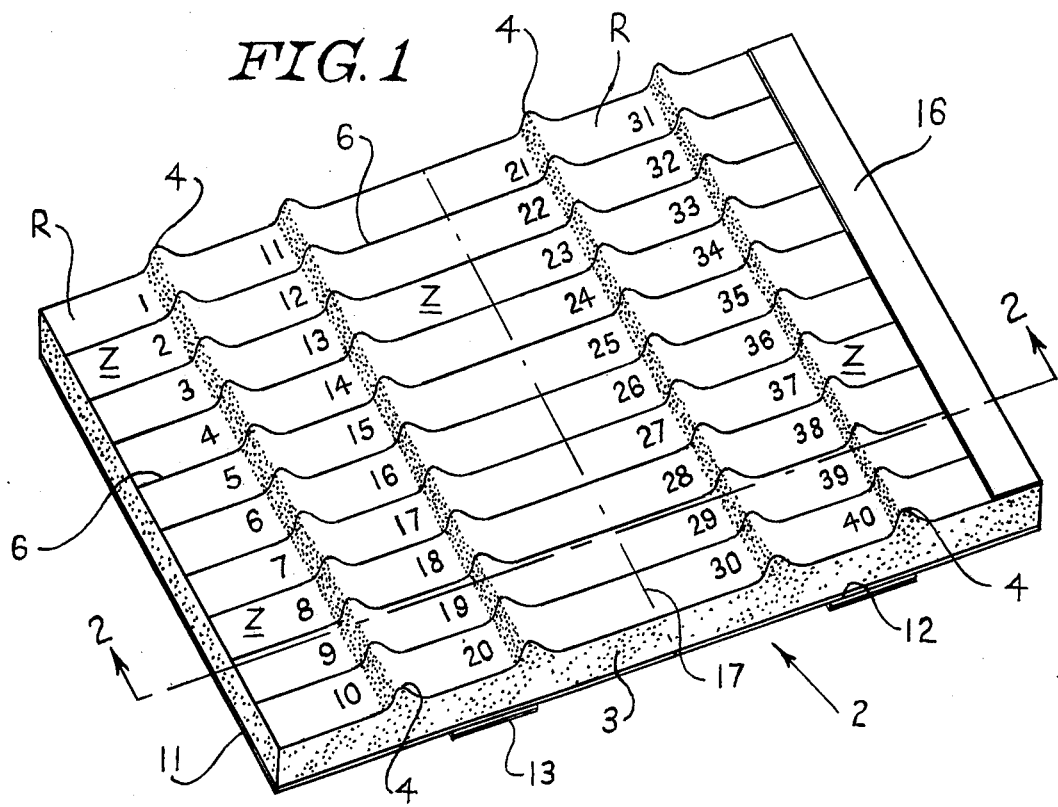
FIG. 1 is an isometric view of the surgical needle retaining and inventory pad hereof.
Figure 2:
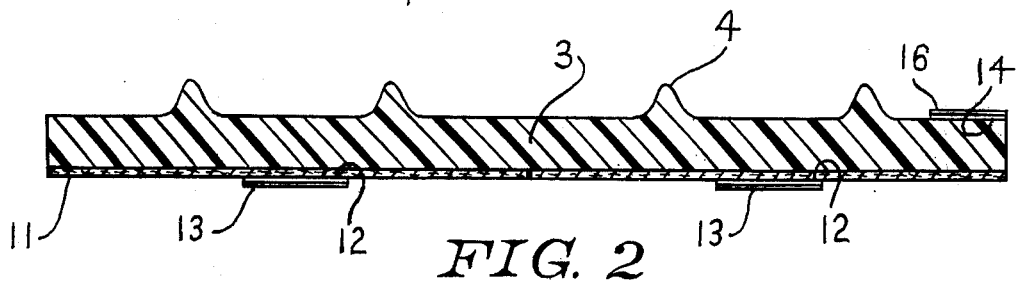
FIG. 2 is a vertical section taken in a plane indicated by line 2—2 in FIG. 1.
Figure 3:
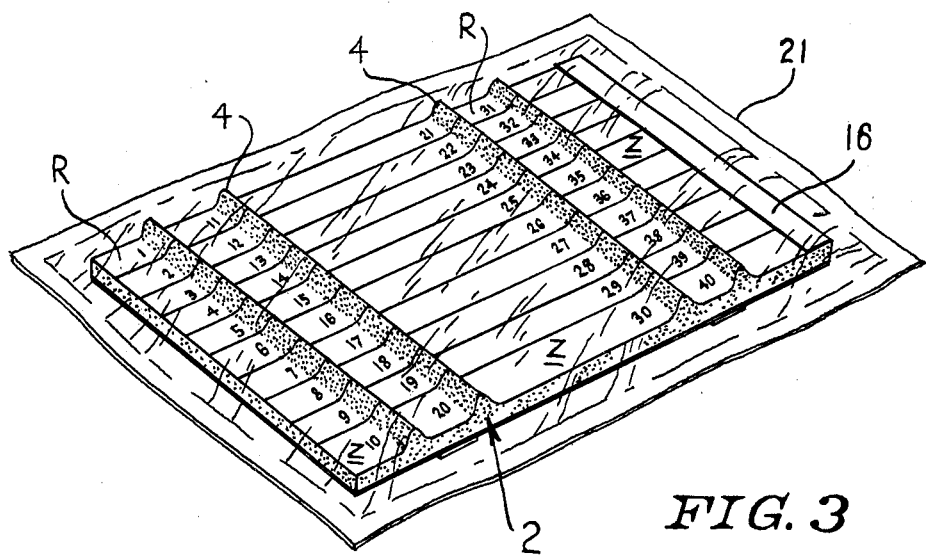
FIG. 3 is an isometric view of the pad as initially packaged in a sterile sealed flexible container.
Figure 4:
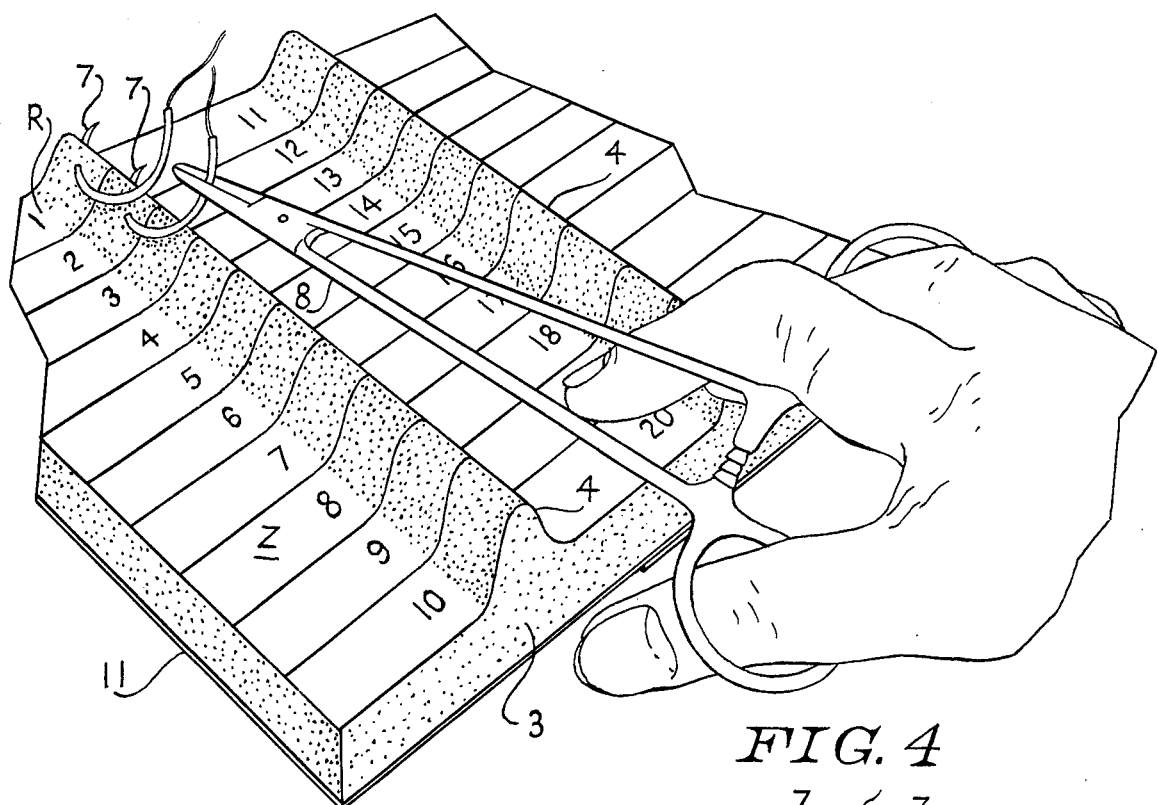
FIG. 4 is a fragmentary isometric view of the pad illustrating how a surgical needle is inserted and held thereby.
Figure 5:
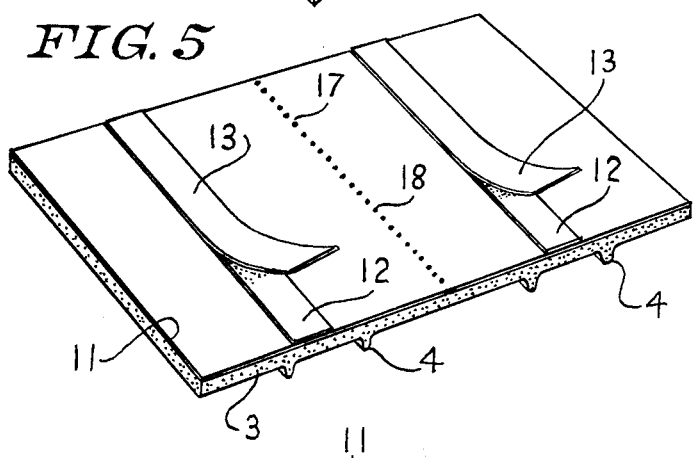
FIG. 5 is an isometric view looking at the back face of the pad.
Figure 6:
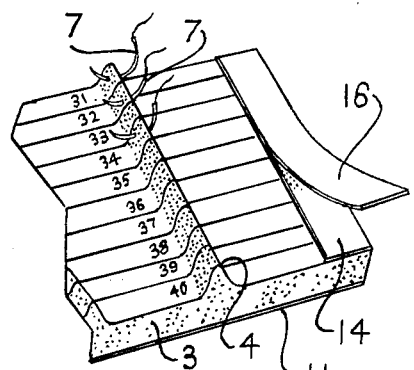
FIG. 6 is a fragmentary isometric view on a reduced scale of a portion of the pad illustrating how consecutive needles which were used in the surgery are held by the pad.

It will be noted that each row of zones (four rows of zones in the preferred embodiment) contains ten zones numbered consecutively in each row. The lines 6 and the zone numbers are marked on the top face of the pad by any suitable printing ink. Each ridge 4 is desirably continuous but it provides a portion thereof adjacent each zone Z into which a surgical needle 7 (FIG. 4) may be laterally inserted by means of the usual instrument such as needle holder 8, and be firmly retained in the ridge.

In use during surgery, when a needle is removed from a patient, it is inserted in the manner described into a ridge adjacent the first needle zone 1 which is marked number 1, and the next needle removed from the patient is inserted in the ridge adjacent the next consecutive zone marked 2. This procedure is continued until all the needles removed from the patient are placed or received on the pad. Since an accurate count of needles dispensed to the surgeon is kept in the usual manner, by merely looking at the pad one can tell after the surgery is completed whether the total number of needles consecutively inserted into the pad is the same as the number of needles dispensed to the surgeon. If so, the patient can be safely closed.

Desirably the pad is provided with at least two spaced apart continuous ridges 4 which provide two rows of zones Z although only one ridge and one row of zones is feasible. Preferably, the pad is formed with four continuous ridges which form four rows of side by side zones with each row having ten zones. Although ridges 4 are integrally formed with base sheet 3, they can be separate pieces adhered by adhesive bonding to the base sheet but this is not as advantageous a construction as the integrally formed ridges. In this connection, it will be noted that ridges 4 are triangularly shaped in cross section which facilitates their formation.

Desirably, to reinforce the pad the back surface face is adhesively bonded to a relatively stiff but flexible backing sheet 11 desirably of 4-ply paperboard. Adhered to the exposed face of the backing sheet are strips 12 of pressure sensitive tape which are normally covered with masking strips 13. When the pad is to be used in surgery these masking strips are removed by hand, and pressure sensitive strips 12 provide means for adhesively holding the pad to a support in the surgery room.

Figure 7:
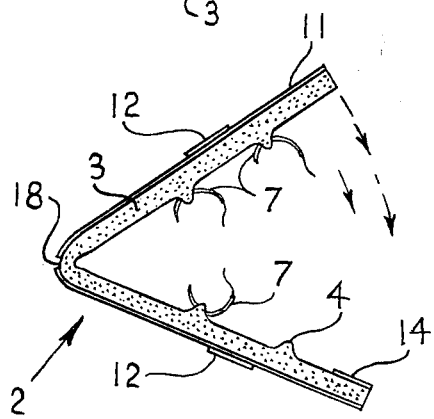
FIG. 7 is a side elevational view illustrating how the pad may be folded on itself.
Figure 8:
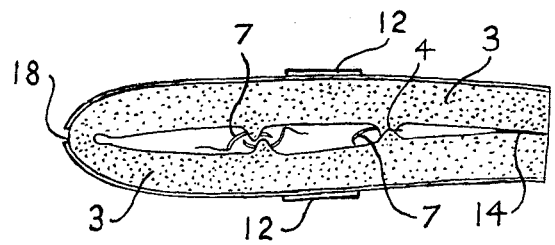
FIG. 8 is a vertical cross section on an enlarged scale of the folded pad in which adjacent edges are adhered together.

Means is provided after the surgery to enable the pad to be folded on itself for disposal with its edges adhered together. For this purpose a strip 14 of pressure sensitive tape is attached to the upper face of the pad adjacent one edge thereof, and is normally covered with a strip of masking tape 16. When the masking tape 16 is removed, pad 2 can be folded upon itself as shown in FIG. 7 to the position shown in FIG. 8 whereat the pressure sensitive tape 14 bonds the two adjacent edges of the pad together, thus rendering the pad completely disposable with the used needles 7 completely incased. To facilitate the folding, backing sheet 11 is provided with a line of weakness 17, desirably a perforation line 18, and the row of zone Z above line 18 is wider than the width of the other rows of zones.

Pad 2 is packaged initially in a transparent sealed and sterilized envelope 21, as is usual with surgical implements. In the embodiment illustrated, the pad is about 8 inches long, about 5 inches wide, about ¼ inch uniform thickness except at ridges 4 which project about ¼ inch above the top face of the sheet and are about ⅜ inch wide at the base.

I claim:

1. A surgical needle retaining and inventory pad comprising a base sheet having at least three parallel rows of consecutively numbered needle receiving zones on a face thereof, and at least two spaced apart continuous ridges of resilient flexible material projecting upright from said face adjacent each zone into which a surgical needle can be inserted and retained, said ridges being integral with said base sheet and parallel to each other, the consecutively numbered zones being defined by the ridges and by lines on said face of the base sheet extending transversely with respect to said ridges, said base sheet being permanently bonded to a relatively stiff backing sheet which has a line of weakness along which the pad can be folded.

2. A surgical needle retaining and inventory pad according to claim 1 wherein said face has a pressure-sensitive strip adjacent one edge of the pad for engaging the opposite edge and retaining the pad in folded condition.

3. The pad of claim 1 wherein the base sheet is of resilient flexible polyurethane foam-like material and has a plurality of side by side rows of such needle receiving zones with the zones consecutively numbered commencing with number one through the number designating the total number of zones, and the ridge of resilient flexible material adjacent each zone is part of a continuous upright ridge between adjacent rows of zones and is integral with said base sheet.

4. A surgical needle retaining and inventory pad comprising a base sheet having at least two side by side ridges of flexible resilient polyurethane foam-like material into which a surgical needle can be inserted and retained, said ridges projecting upright from a face of the pad, and a plurality of lines marked on said face extending transversely across said ridges dividing said face into a plurality of side by side rows of needle receiving zones with each row adjacent a ridge, the zones being marked with consecutive numbers commencing with number one through the number designating the total number of zones, said base sheet having at least three parallel rows of said consecutively numbered needle receiving zones, and at least two spaced apart continuous ridges integral with said base sheet and parallel to each other; the consecutively numbered zones being defined by the ridges and by lines on said face of the base sheet extending transversely with respect to said ridges, the opposite face of said base sheet being permanently bonded to a relatively stiff backing sheet which has a line of weakness along which the pad can be folded.

5. The surgical needle pad of claim 4 wherein the pad and ridges are integrally formed, and each of the ridges has a substantially triangular cross sectional shape.

* * * * *